(12) United States Patent
Ounanian et al.

(10) Patent No.: US 9,415,243 B2
(45) Date of Patent: Aug. 16, 2016

(54) PARTICLE-FREE MICRODERMABRASION FORMULATIONS

(71) Applicant: Micdermco, L.L.C., Dallas, TX (US)

(72) Inventors: Hovig Ounanian, Denton, TX (US); Lisa Cohorn, Dallas, TX (US)

(73) Assignee: Micdermco, L.L.C., Dallas, TX (US)

( * ) Notice: Subject to any disclaimer, the term of this patent is extended or adjusted under 35 U.S.C. 154(b) by 25 days.

(21) Appl. No.: 14/183,079

(22) Filed: Feb. 18, 2014

(65) Prior Publication Data

US 2015/0231059 A1   Aug. 20, 2015

(51) Int. Cl.
| | |
|---|---|
| *A61Q 19/10* | (2006.01) |
| *A61K 8/41* | (2006.01) |
| *A61K 8/49* | (2006.01) |
| *A61K 8/92* | (2006.01) |
| *A61K 8/19* | (2006.01) |

(52) U.S. Cl.
CPC . *A61Q 19/10* (2013.01); *A61K 8/19* (2013.01); *A61K 8/41* (2013.01); *A61K 8/4973* (2013.01); *A61K 8/4993* (2013.01); *A61K 8/922* (2013.01); *A61K 2800/28* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 4,529,605 A * | 7/1985 | Lynch et al. | 514/552 |
| 4,988,502 A | 1/1991 | Ounanian et al. | |
| 5,049,376 A | 9/1991 | Murphy et al. | |
| 5,290,543 A | 3/1994 | Ounanian et al. | |
| 5,738,856 A * | 4/1998 | Korb | A61K 8/375 424/401 |
| 6,942,649 B2 | 9/2005 | Ignon et al. | |
| 7,025,976 B2 | 4/2006 | Fox et al. | |
| 7,482,314 B2 | 1/2009 | Grimes et al. | |
| 7,687,065 B1 * | 3/2010 | Maor et al. | 424/401 |
| 7,951,156 B2 | 5/2011 | Karasiuk | |
| 8,084,409 B2 | 12/2011 | Lucka et al. | |
| 2002/0086039 A1 | 7/2002 | Lee et al. | |
| 2003/0049291 A1 | 3/2003 | Cheski | |
| 2004/0011993 A1 * | 1/2004 | Ficken et al. | 252/189 |
| 2005/0169868 A1 | 8/2005 | Mohammadi et al. | |
| 2005/0197407 A1 | 9/2005 | DiNardo et al. | |
| 2005/0281771 A1 * | 12/2005 | Bunker | 424/70.13 |
| 2007/0189989 A1 | 8/2007 | Cantwell et al. | |
| 2007/0253914 A1 | 11/2007 | Ha et al. | |
| 2007/0280976 A1 * | 12/2007 | Taylor et al. | 424/401 |
| 2009/0104174 A1 | 4/2009 | Smith | |
| 2011/0008271 A1 | 1/2011 | Ounanian et al. | |
| 2012/0288458 A1 * | 11/2012 | Yamaguchi et al. | 424/60 |
| 2013/0039869 A1 | 2/2013 | Ramirez et al. | |
| 2014/0134119 A1 | 5/2014 | Faryniarz et al. | |

FOREIGN PATENT DOCUMENTS

| | | |
|---|---|---|
| WO | 9219215 | 11/1992 |
| WO | WO 2007/029982 A1 * | 3/2007 |

OTHER PUBLICATIONS

Long "How to get balanced skin" published online Feb. 23, 2011; http://www.elle.com/beauty/makeup-skin-care/how-to-get-balanced-skin-539785.*

* cited by examiner

*Primary Examiner* — Jyothsna Venkat
(74) *Attorney, Agent, or Firm* — David W. Carstens; Shaukat A. Karjeker; Carstens & Cahoon, LLP

(57) ABSTRACT

An exemplary embodiment provides a particulate-free microdermabrasion formulation that includes a emulsifying agent; an ionic salt; a moisturizer; a neutralizer; and water. The formulation is free of acids, abrasive particulates, and enzymes. Further, upon application of the formulation to the skin surface, the formulation forms a thin layer that coats the skin surface and penetrates into pores of the skin. The thin layer sloughs off upon light rubbing, for example by hand or with a soft cloth or wipe, thereby removing dead skin cells and debris from the skin surface to leave a smooth, moisturized newly exposed skin surface.

12 Claims, 2 Drawing Sheets

PARTICLE-FREE MICRODERMABRASION FORMULATIONS

BACKGROUND

1. Field of the Invention

The technology relates to the field of cosmetic chemistry, and more particularly to formulations that are useful, for example, in the removal of "dead" skin cells from the epidermis, commonly known as exfoliant or microdermabrasion formulations and that may also have other functions, such as moisturizing the skin.

2. Description of the Related Art

According to a report at www.info.ibtpartners.com, the field of cosmetics is a growth sector globally. The article which was published on May 20, 2013, states: "The global cosmetics industry is estimated to be worth $495 billion in 2012. Growth has clearly come from expanding geographic markets: India is reckoned to be growing at +15% per annum while the Chinese market could overtake Japan within 5 years. But growth is also coming from newly defined sectors: anti-aging, men's care, sun care, organic cosmetics and the so-called "cosmeceuticals" to name the most obvious. These sectors appeal to a growing audience, including Baby-boomers, Gen X-ers, and increasingly, Gen Y-ers.

Several of the niche-markets identified in the above report, and perhaps especially the well-heeled "Baby-boomers," have shown a desire to improve the appearance and condition of their skin through the use of anti-wrinkle or "anti-aging" formulations, moisturizers, exfoliants, and more recently, microdermabrasion treatments, as a sub-category of exfoliant treatment. In general, any treatment that removes the outer layer of dead skin cells to expose "new skin" beneath may be classified as a exfoliant treatment. Usually, the exfoliation is carried out through either chemical or mechanical means, or a combination of both. In the chemical exfoliant formulations, the more typically used active chemical agent may be an acid, such as salicylic acid, glycolic acid, citric acid, or malic acid. The alpha and beta hydroxy acids are also known to be useful in exfoliation. Fruit enzymes may also be used as the active chemical agent. In its mechanical aspect, exfoliation usually involves the use of an abrasive which includes particulates of a particular size and type. Examples of such mechanical exfoliant formulations use the abrasive properties of particulates such as salt crystals, pumice, volcanic rock, crushed apricot kernels or almond shells, crystalline sugar, oats, and natural or synthetic micro-beads. In other mechanical treatments abrasive materials may also be used, such as loofah sponges, brushes, microfiber cloth, crepe paper, and the like that have a texture that promotes mechanical removal of dead skin cells during scrubbing.

Microdermabrasion has in the past typically been a mechanical abrasion technique used by professionals in med spas, physician's offices, and in salons to remove the outermost layer of dead skin cells from the epidermis, while using a suction machine to lift up the skin during exfoliation. More recently, the term microdermabrasion has also been applied to over the counter formulations that include fine particulates that are capable of performing a mechanical exfoliation.

There are several examples of particulate-containing formulations in the patent literature. For example, U.S. Pat. No. 7,025,976 uses a crystalline emulsion that includes coated crystals in a carrier to carry out microdermabrasion. U.S. Pat. No. 7,482,314 has a microdermabrasion composition that includes surfactant (20-60%), volatile silicone oil (5-60%), an anhydrous solvent, and 1-25% of a (water-soluble) salt. The water-soluble salt is not dissolved, but is present at a particle size of 50 to 2000 microns and acts as an abrasive. U.S. Pat. No. 8,084,409 is directed to a microdermabrasion soap that has about 15% of an abrasive compound, such as magnesium oxide, in a particle size of 120 to 200 microns. US Patent Application Publication 2002/0086039 is directed to microdermabrasion formulations that include bio-glass, or hydroxyapatite. The bio-active glass and hydroxyapatite are in particulate form. US Patent Application Publication 2003/0049291 is directed to a cream that contains abrasive particles, and the cream is asserted as useful in microdermabrasion. US Patent Application Publication 2005/0169868 is directed to an exfoliating composition that includes at least three insoluble particulate ingredients that are abrasive.

A concern in the use of microdermabrasion formulations and devices, regardless of source, is the potential for skin irritation and discomfort from applied chemicals, such as acids and enzymes. Some abrasive particles may also raise concerns regarding skin irritation or discomfort. Further, harsh abrasion may also damage underlying "new skin" during removal of the upper dead skin cells, especially if not carefully controlled by an experienced skin-care professional. Moreover, once new skin is exposed, the new skin may rapidly "dry out" and become damaged. To avoid such drying out and damage, microdermabrasion treatment may be immediately followed by the application of formulations that are intended to moisturize, soothe and/or reduce the potential for the newly-exposed skin to rapidly lose moisture.

SUMMARY

The following is a summary of some aspects and exemplary embodiments of the present technology, of which a more detailed explanation is provided under the Detailed Description section, here below.

An exemplary embodiment provides a particulate-free microdermabrasion formulation that includes an emulsifier; an ester or a natural oil (preferably organic); a viscosity increasing agent, an ionic salt; a neutralizer; and water. In exemplary embodiments, the formulation is free of any one, or all of: acids, hydroxy acids, abrasive particulates, vitamins, and enzymes. Further, upon application of the formulation to the skin surface, the formulation forms a thin layer that both coats the skin surface and that also penetrates into pores of the skin. The thin layer is allowed to dwell on the skin for a period of time, up to about 3 to about 5 minutes. The thin layer sloughs off upon light rubbing, for example by hand or with an applicator, for example that may include a soft cloth, or wipe. The light rubbing action removes dead skin cells and debris from the skin surface. Optionally, the exemplary embodiment of the particulate-free microdermabrasion formulation may include nonionic surfactants and emulsifiers.

Exemplary surfactants include the class known as emulsifiers. Examples of the useful surfactants include, but are not limited to: polyoxythylene sorbitan, sorbitan stearate, isononyl isononaonate, ethylhexyl isononaonate, Abietic Acid, Beeswax, Bis-Peg-15 Methyl Ether Dimethicone, Butylene Glycol Stearate, Cetyl PEG/PPG-10/1 Dimethicone, Coceth-25, C12-15 Pareth-5, Dimethicone PEG/PPG-12/4, Glycereth-6 Laurate, Hydrogenated vegetable Glyceride, Isosteareth-20, Myreth-10, Nonoxynol-14, Olive Oil PEG-7 Esters, PEG-20 Castor Oil, PEG-30 Sorbitan Tetraoleate, Polaximine 1102, Polyglyceryl-10 Laurate, Polysorbate 60, Propylene Glycol, Ricinoleate, Sodium Palmitate, Sorbitan Stearate and the like.

The exemplary viscosity increasing agent (also known as a "thickening agent") may be selected from a list that includes but is not limited to: hydrophilic polymer compositions, such as the polyacrylate polmer gels and the like, Agar, Bentonite, Carbomer, Dimethicone/PEG-10 Crosspolymer, Gelatin, Hectorite, Lauryl Alcohol, Magnesium Aluminum Silicate, Pectin, Sodium Acrylate Copolymer, Tapioca Starch, and Xanthan Gum. In an exemplary embodiment, the viscosity increasing agent may be Carbomer, which is a cross linked polyacrylate hydrophilic polymer composition, a version of which is sold commercially under the trademark Carbopol® 934 (by Lubrizol of Cleveland, Ohio), or its equivalent.

In exemplary embodiments, the ionic salt may be selected from, for example, sodium chloride, potassium chloride, and the like. The salt is not present in such concentration and at such coarseness as to effect dermabrasion when the particulate-free microdermabrasion formulation is applied to skin, or when it is rubbed off the skin. Accordingly, it is not in "particulate" form.

An exemplary neutralizer of the exemplary particulate-free microdermabrasion formulation is effective to achieve and maintain a pH of about 7.0, or between about 6.0 and about 8.0. The neutralizer may be selected from a list that includes, but is not limited to: tri-ethanolamine, Acetic Acid, Benzoic Acid, Calcium Hydroxide, Diisopropanolamine, Ethanolamine, Glycolic Acid, Hydrochloric Acid, Lactic Acid, Magnesium Hydroxide, Potassium Hydroxide, Sodium Bicarbonate, and the like. While this list includes acids, the acids are added only in sufficient quantity to perform a neutralizing function, and any residual acids after neutralization in so insignificant in such quantity or concentration that it does not materially affect the skin or to engage in any form of microdermabrasion skin treatment. Accordingly, the particulate-free microdermabrasion formulation is said to be "free of acids," because acid concentration, if any, does not perform a skin treatment function but is merely residual acid after neutralization, if acid is used as a neutralizer.

Optionally, the exemplary embodiment of the particulate-free microdermabrasion formulation further includes a skin moisturizing composition, also known as an "emollient." The optional moisturizing composition includes but is not limited to: light, non-toxic, non-irritating oil, such as almond oil Arachidyl Propionate, Behenyl Benzoate, C12-15 Alkyl Benzoate, Decyl Oleate, Ethylhexyl Isonanoate, Fish Glycerides, Glyceryl Alginate, Hexyldecanol, Isononyl Isonanoate, Lauryl Cocoate, Methyl Caprylate, Nonyl Acetate, Oleyl Alcohol, Pentaerythrityl Rosinate, Stearyl Benzoate, Tocopheryl Glucoside, and Wheat Germ Glycerides.

Further optionally, exemplary embodiments of the particulate-free microdermabrasion formulation may include a bactericide, such as but not limited to: benzyly alcohol, glyceryl caprylate, glyceryl undeclynate, phenoxyethanol, and the like. It may also include a cosmetics preservative, such as potassium sorbate, for example.

Exemplary embodiments of the particulate-free microdermabrasion formulation may also include a humectant. Examples of skin conditioning humectants include, but are not limited to: Aloe Barbadensis Leaf Extract, Butanediol, Chitosan PCA, Diglycerin, Ethyl Glucoside, Fructose, Glycereth-26, Lycine PCA, Mannitol, Polyglycerin-20, Sodium PCA, Urea, and Xylitol.

Exemplary embodiments of the particulate-free microdermabrasion formulation may also include an occlusive agent. The occlusive agents include, but are not limited to: Arachidyl Behenate, Butter, Canola Oil, cotton seed oil, Dimethicone, Glycol Dilaurate, Hydrogenated Shea Butter, Isocetyl Behenate, Lauryl Stearate, Methicone, Neopentyl Glycol Stearate, Octyldodecyl Myristate, *Prunus Amygdalua Dulcis* (Sweet Almond) Oil, *Ricinus Communis* (Castor) Seed Oil, Shea Butter Cetyl Esters, Squalane, Tocopherol, and *Zea Mays* (Corn) Oil.

Exemplary embodiments of the particulate-free microdermabrasion formulation may include miscellaneous ingredients that enhance the appearance of dry and damaged skin, and that reduce flakiness of the skin, and restore suppleness. These include, but are not limited to: Acetyl Carnitine, Beeswax, Calcium Gluconate, Darutoside, Elastin, *Ginko Biloba* Leaf Extract, *Hamamelis Virginiana* (Witch Hazel) Water, Jojoba Alcohol, Keratin Amino Acids, Lanesterol, Magnesium Ascorbate, Niacinamide, Oat Amino Acids, Palmitoyl Carnitine, Quercetin, Retinol, Sea Salt, Tallow Betaine, Ubiquinone, Wine, and Yeast Palmitate Another exemplary embodiment provides a particulate-free microdermabrasion formulation that includes a viscosity increasing agent that is selected from the hydrophilic polymer compositions, and which is effective as a stabilizer and thickener. The formulation also includes an ionic salt; a neutralizer; a skin moisturizing composition; and water. The formulation has a pH in the range about 6 to about 8, and is free of acids, abrasive particulates, and enzymes. Further, upon application of the formulation to the skin surface, the formulation forms a thin layer that coats the skin surface and that penetrates into pores of the skin. The thin layer sloughs off upon light rubbing, for example by hand or with a soft cloth or wipe, thereby removing dead skin cells and debris from the skin surface while leaving smooth moisturized exposed new skin.

A further exemplary embodiment provides a particulate-free microdermabrasion formulation that includes a hydrophilic polymer composition which includes a cross-linked polyacrylate gel effective as a stabilizer and thickener. It further also contains a neutralizer that includes tri-ethanolamine; an ionic salt; a nonionic surfactant; a skin moisturizing composition; and water. The formulation forms a thin layer on the surface that penetrates into pores of the skin surface. The thin layer sloughs off upon light rubbing thereby removing dead skin cells and debris from the skin surface. Debris and dead skin cells are sloughed-off the skin in substantially cylindrical-shaped fragments (of the layer) to leave smooth and moisturized exposed new skin.

An exemplary embodiment of particle-free microdermabrasion formulation can be used on all skin tones where other microdermabrasion formulations may cause discoloration or otherwise affect skin tone or uniformity of tone. Thus, the formulation does not adversely affect skin tone, or cause skin discoloration or redness. The exemplary formulations are safe enough for daily use, and yet effectively clean and remove make-up and other debris, such as pollutants from environment left on the skin. Exemplary embodiments of the formulation are an all-in-one product for skin renewal, refreshing and conditioning for all skin types.

In an exemplary embodiment, the formulation is free of chemical skin-irritants, and free of chemical compositions that are intended to inhibit skin irritation, such as idebenone and/or its derivatives.

BRIEF DESCRIPTION OF THE DRAWINGS

Various embodiments will be described in conjunction with the following drawings which are schematic, not to scale, and wherein like numerals denote like elements, and.

DETAILED DESCRIPTION OF EXEMPLARY EMBODIMENTS

Figure 1:
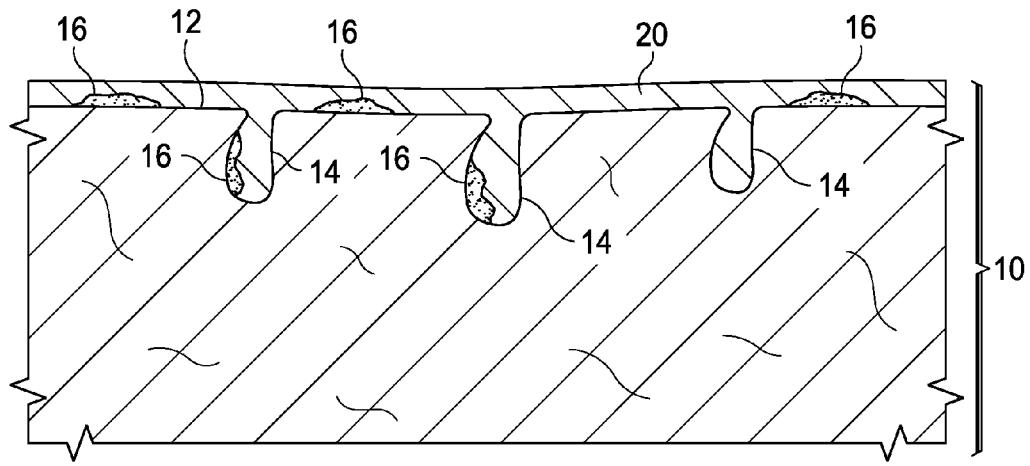
FIG. 1 is an illustrative view of an exemplary embodiment of a formulation applied to the upper surface of skin that includes pores and dead skin cells.

The following provides a detailed description of exemplary embodiments of the particle-free microdermabrasion formulations. It should be understood that describing examples of these embodiments facilitates an understanding of the inventions, but the exemplary embodiments do not limit the scope of the inventions in any way. The inventions are demarcated only by the claims appended here below.

Microdermabrasion systems typically include either a chemical that strips dead skin cells from the upper surface of the epidermis to expose new skin cells, or use a mechanical abrasion technique to "scrub" dead skin cells from the epidermis, or use both a chemical as well as mechanical abrasion to remove dead skin cells.

The present technology presents exemplary microdermabrasion formulations that are free of particulates, whether abrasive, non-abrasive, natural, or synthetic. Moreover, exemplary embodiments are also free of acids, enzymes, and "chemical skin irritants." In the specification and claims, the term "chemical skin irritant" broadly includes those chemical compositions that are either known to cause skin irritation in most persons that undergo microdermabrasion or that are reasonably suspected by skin care professionals as likely to cause skin irritation or inflammation in a significant proportion of the population that undergoes microdermabrasion. Non-limiting examples of chemical skin irritants include: carboxylic acids, such as alpha hydroxy acids and beta hydroxy acids, salicylic acid, oxalic acid, malic acid, gluconic acid, and the like; phenol, benzoyl peroxide, retinol, enzymes (whether natural or synthetic), and the like.

Since acid may be used as a pH neutralizer in the particulate-free microdermabrasion formulations, there may be a small and insignificant amount of residual acid in the formulations. The term "free of acid" or "acid free" in reference to the particulate-free microdermabrasion formulations does not exclude the presence of insignificant residual amounts of neutralizing acids. An insignificant amount or concentration is one that does not materially affect the skin or to engage in any form of microdermabrasion skin treatment. Accordingly, the particulate-free microdermabrasion formulation is said to be "free of acids," because acid concentration, if any, does not perform a skin treatment function but is merely residual acid after neutralization, if acid is used as a neutralizer.

An exemplary embodiment of the particulate-free microdermabrasion formulation is also free of vitamins, or like asserted "dietary nutrient supplements," as active components.

Exemplary embodiments of the particulate-free microdermabrasion formulations may be liquid, such as lotions dispensed, for example from squeeze tubes, pump bottles, or aerosol-type containers or may be creams dispensed in jars. Further, the formulations may be supplied on pre-impregnated wipes, or applicators that may be disposable, for convenience. Applicators may include a variety of devices, including but not limited to, for example, simple spatulas, and rotary brush head devices.

Exemplary embodiments of the particulate-free microdermabrasion formulations do not require heating to a higher temperature, and may be applied to the skin at "room temperature," which is typically in the range about 15 to about 30° C., and is often typically controlled at 18 to 25° C.

In general, the skin surface (epidermis) of the party to be treated with the particulate-free formulations for microdermabrasion does not have to be pre-treated in any special way. It is prudent, however, to wash off any loose surface dirt, grime and oil by bathing showering, or washing the skin area to be treated with the formulation in a normal manner with soap, or body wash, as applicable, to minimize potential interference with the activity of the formulation, and obtain the best results. Chemical pretreatment of the skin area is not necessary. Exemplary particulate-free formulations are gentle to the skin and non-irritating, and may be used on the hands, feet, décolleté, neck area, body and face. It is preferred that the skin be gently dried prior to applying the formulation.

The particulate-free microdermabrasion formulation is gentle to the skin, and exemplary formulations may be used daily. The exemplary formulation not only removes dead skin cells, but also effectively cleans make-up residue, other skin treatment products, and pollutants from the skin, and conditions the skin. In an exemplary embodiment, the particulate-free microdermabrasion formulation is applied to the skin surface and allowed to dwell on the surface for from about 2 to about 5 minutes before being removed by rubbing gently with hand, cloth or applicator to slough off the formulation.

An exemplary embodiment provides a particulate-free microdermabrasion formulation that includes a viscosity increasing agent, which is effective as a stabilizer and thickener; an ionic salt; a neutralizer; and water. In an exemplary embodiment, the formulation is free of any one, or all of: acids, hydroxy acids, abrasive particulates, vitamins, and enzymes. Further, upon application of the formulation to the skin surface, the formulation forms a thin layer that coats the skin surface and that also penetrates into pores of the skin. The thin layer sloughs off upon light rubbing, for example by hand or with an applicator, for example that includes a soft cloth, or a wipe, or a rotary brush head, without limitation. The light rubbing action removes dead skin cells and debris from the skin surface.

Figure 2:
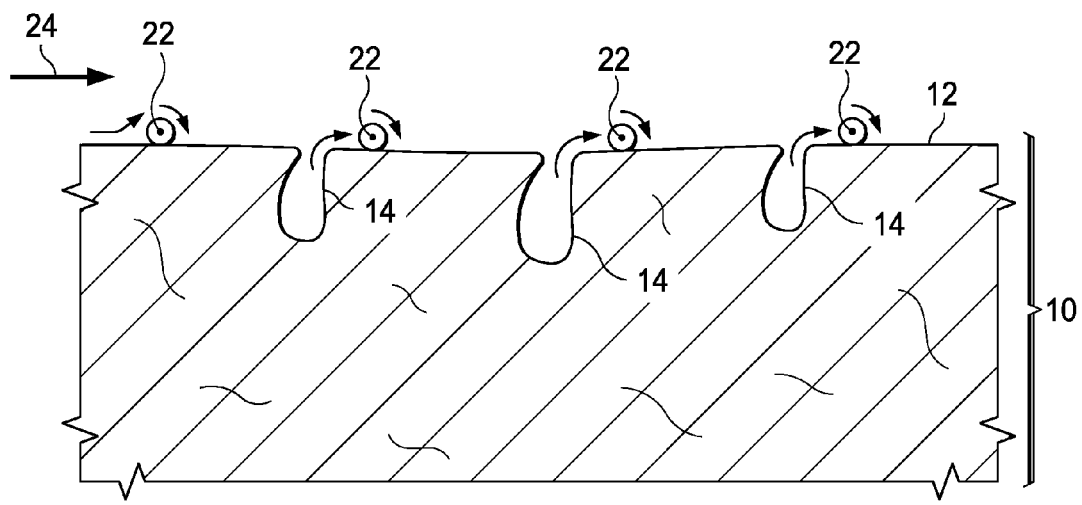
FIG. 2 is an illustrative view of an exemplary embodiment of a formulation being removed from the skin by light sloughing off action to form elongate crumbs that include removed dead skin cells and other debris removed from the skin surface and pores.

In the exemplary embodiment illustrated in FIGS. 1 and 2, a particulate-free microdermabrasion formulation 20 is applied in a thin layer over a surface 12 of skin 10. The skin 10 is representationally shown only to facilitate explaining features of the exemplary embodiments, and so unnecessary anatomical detail of the skin is omitted. The skin 10 has several open pores 14. The outer skin surface 12 and the pores include any of grime and dead skin cells (all generically "debris"), all represented by numeral 16. The formulation 12 covers the debris 16 on the skin surface and fills the pores to contact debris trapped within the pores. After the formulation has dwelled on the skin for at least about 2 minutes, and up to about 10 minutes, it may be removed by rubbing by hand, or with a soft cloth, or wipe, or with an applicator in the direction shown by arrow 24, for example. This rubbing action tangential to the skin surface causes the formulation to peel away from the skin surface 12 and to be pulled out of the pores thereby unclogging the pores, as indicated by arrows in FIG. 2, and to form small substantially cylindrical fragments 22 that can be brushed off the skin 12. The removal of the formulation in this manner provides gentle and safe particle-free microdermabrasion leaving the skin and pores clean and the skin surface feeling conditioned, smoothed and renewed. The exemplary particle-free microdermabrasion formulation can be used on all skin tones where other microdermabrasion formulations may cause discoloration or otherwise affect skin tone or uniformity of tone. Thus, the formulation does not affect skin tone, or cause skin discoloration or redness.

The surfactant preferably but not necessarily includes those emulsifying agents employed in cosmetics to prepare emulsions, and that are free of skin irritant issues. The efficacy of emulsifying agent depends on their ability to reduce surface tension, to form complex films on the surface of emulsified droplets and to create a repulsive barrier on emulsified droplets to prevent their coalescence. An exemplary emulsifier and/or surfactant may be selected from the following non-limiting examples: Abietic Acid, Beeswax, Bis-Peg-15 Methyl Ether Dimethicone, Butylene Glycol Stearate, Cetyl PEG/PPG-10/1 Dimethicone, Coceth-25, C12-15 Pareth-5, Dimethicone PEG/PPG-12/4, Glycereth-6 Laurate, Hydrogenated vegetable Glyceride, Isosteareth-20, Myreth-10, Nonoxynol-14, Olive Oil PEG-7 Esters, PEG-20 Castor Oil, PEG-30 Sorbitan Tetraoleate, Polaximine 1102, Polyglyceryl-10 Laurate, Polysorbate 60, Propylene Glycol, Ricinoleate, Sodium Palmitate, and Sorbitan Stearate. Emulsifiers may be present in the range from about 0.10 wt. % to about 10.0 wt. %, or more, if necessary to cause the formation of a homogenous emulsion.

Viscosity increasing agents are used to thicken the aqueous portions of cosmetic products. Their ability to perform this function is related to their water solubility or hydrophilic nature acting as a viscosity increasing agent may be selected from a list that includes, but is not limited to: hydrophilic polymer compositions, such as the polyacrylate polmer gels and the like, Agar, Bentonite, Carbomer, Dimethicone/PEG-10 Crosspolymer, Gelatin, Hectorite, Lauryl Alcohol, Magnesium Aluminum Silicate, Pectin, Sodium Acrylate Copolymer, Tapioca Starch, and Xanthan Gum. In an exemplary embodiment, the viscosity increasing agent may be a hydrophilic polymer composition, such as Carbomer [e.g., Carbopol® 934 (sold by Lubrizol of Cleveland, Ohio), or its equivalent]. The viscosity increasing agent may be added to achieve the consistency of the desired product, for example, a fluid lotion or a more creamy texture. In general, about 0.1 wt % to about 7.5 wt. % of a suitable viscosity increasing agent may be found useful.

In exemplary embodiments, the ionic salt may be selected from, for example, sodium chloride, potassium chloride, and the like. The salt is not present in such concentration and at such coarseness as to perform dermabrasion, when the particulate-free microdermabrasion formulation is applied to skin, or when it is rubbed off the skin. Accordingly, it is not in particulate form, and does not act as a skin-abrasive. The amount of the ionic salt may be in the range from about 0.1 wt. % to about 5.0 wt. %, and preferably about 0.1 wt. % to about 2.5 wt. %.

The exemplary particulate-free microdermabrasion formulation may include a pH neutralizer present in quantity sufficient to achieve and maintain a pH of about 7.0, or between about 6.0 and about 8.0. The neutralizer may be selected from a list that includes, but is not limited to: tri-ethanolamine, Acetic Acid, Benzoic Acid, Calcium Hydroxide, Diisopropanolamine, Ethanolamine, Glycolic Acid, Hydrochloric Acid, Lactic Acid, Magnesium Hydroxide, Potassium Hydroxide, Sodium Bicarbonate, and the like. While this list includes acids, the acids are added only in sufficient quantity to perform a neutralizing function, and any residual acids after neutralization in so insignificant in such quantity or concentration that it does not materially affect the skin or to engage in any form of microdermabrasion skin treatment. Accordingly, the particulate-free microdermabrasion formulation is said to be "free of acids," because acid concentration, if any, does not perform a skin treatment function but is merely residual acid after neutralization, if acid is used as a neutralizer.

Exemplary embodiments of the particulate-free microdermabrasion formulation may further include a skin moisturizing composition, also known as an emollient. Emollients are cosmetic ingredients which help to maintain the soft, smooth and pliable appearance of skin. Emollients function by their ability to remain on the skin surface to act as lubricants, to reduce flaking and to improve the skin's appearance. The moisturizing compositions include, but are not limited to: light, non-toxic, non-irritating oils and esters, such as almond oil Arachidyl Propionate, Behenyl Benzoate, C12-15 Alkyl Benzoate, Decyl Oleate, Ethylhexyl Isonanoate, Fish Glycerides, Glyceryl Alginate, Hexyldecanol, Isononyl Isonanoate, Lauryl Cocoate, Methyl Caprylate, Nonyl Acetate, Oleyl Alcohol, Pentaerythrityl Rosinate, Stearyl Benzoate, Tocopheryl Glucoside, and Wheat Germ Glycerides. The natural organic oils are preferred. The moisturizing composition may include a mixture of several oils and/or esters, as desired. Typically the formulations may include from about 25 wt. % to about 50 wt. % of the moisturizing compositions.

An exemplary embodiment of the particulate-free microdermabrasion formulation may include the emulsifier class of nonionic, cationic and ionic surfactants. Exemplary surfactants and emulsifiers include, but are not limited to: polyoxythylene sorbitan, sorbitan stearate, isononyl isononaonate, ethylhexyl isononaonate, Abietic Acid, Beeswax, Bis-Peg-15 Methyl Ether Dimethicone, Butylene Glycol Stearate, Cetyl PEG/PPG-10/1 Dimethicone, Coceth-25, C12-15 Pareth-5, Dimethicone PEG/PPG-12/4, Glycereth-6 Laurate, Hydrogenated vegetable Glyceride, Isosteareth-20, Myreth-10, Nonoxynol-14, Olive Oil PEG-7 Esters, PEG-20 Castor Oil, PEG-30 Sorbitan Tetraoleate, Polaximine 1102, Polyglyceryl-10 Laurate, Polysorbate 60, Propylene Glycol, Ricinoleate, Sodium Palmitate, Sorbitan Stearate and the like. In general, the exemplary formulations may include from about 5.0 wt. % to about 7.5 wt. % of the emulsifier.

Further optionally, exemplary embodiments of the particulate-free microdermabrasion formulation may include a bactericide, such as such as but not limited to: benzyly alcohol, glyceryl caprylate, glyceryl undeclynate, phenoxyethanol, and the like. It may also include a cosmetics preservative, such as potassium sorbate, for example.

Exemplary embodiments of the particulate-free microdermabrasion formulation may also include a humectant. Examples of skin conditioning humectants include, but are not limited to: Aloe Barbadensis Leaf Extract, Butanediol, Chitosan PCA, Diglycerin, Ethyl Glucoside, Fructose, Glycereth-26, Lycine PCA, Mannitol, Polyglycerin-20, Sodium PCA, Urea, and Xylitol.

Exemplary embodiments of the particulate-free microdermabrasion formulation may also include an occlusive agent. These are cosmetic ingredients which retard the evaporation of water from the skin by blocking the evaporative loss of water. As a result, occlusive materials increase the water content of the skin. Occlusive agents are generally lipids which tend to remain on the skin. Exemplary occlusive agents include, but are not limited to: Arachidyl Behenate, Butter, Canola Oil, cottonseed oil, Dimethicone, Glycol Dilaurate, Hydrogenated Shea Butter, Isocetyl Behenate, Lauryl Stearate, Methicone, Neopentyl Glycol Stearate, Octyldodecyl Myristate, *Prunus Amygdalua Dulcis* (Sweet Almond) Oil, *Ricinus Communis* (Castor) Seed Oil, Shea Butter Cetyl Esters, Squalane, Tocopherol, and *Zea Mays* (Corn) Oil. In exemplary embodiments, these occlusive agents may be present in amounts ranging from about 13.5 wt. % to about 25.0 wt. %. In other exemplary embodiments, the amounts may range from about 6.5 wt. % and up to about 20 wt. %.

Exemplary embodiments of the particulate-free microdermabrasion formulation may optionally include miscellaneous ingredients that enhance the appearance of dry and damaged skin, and that reduce flakiness of the skin, and restore suppleness. These include, but are not limited to: Acetyl Carnitine, Beeswax, Calcium Gluconate, Darutoside, Elastin, *Ginko Biloba* Leaf Extract, *Hamamelis Virginiana* (Witch Hazel) Water, Jojoba Alcohol, Keratin Amino Acids, Lanesterol, Magnesium Ascorbate, Niacinamide, Oat Amino Acids, Palmitoyl Carnitine, Quercetin, Retinol, Tallow Betaine, Ubiquinone, Wine, and Yeast Palmitate. In general, these optional ingredients may be added in amounts as needed to make exemplary formulations. These ingredients are generally not added in large amounts, but only in sufficient amounts regarded as necessary to achieve the stated purpose of the ingredient with respect to skin condition or treatment.

Another exemplary embodiment provides a particulate-free microdermabrasion formulation that includes a hydrophilic polymer composition, which is effective as a stabilizer and viscosity increasing agent; an ionic salt; a neutralizer; a skin moisturizing composition; and water. The formulation has a pH in the range about 6 to about 8, and is free of acids, free of abrasive particulates, and free of enzymes. Further, upon application of the formulation to the skin surface, the formulation forms a thin layer that coats the skin surface and that penetrates into pores of the skin. The thin layer sloughs off upon light rubbing, for example by hand or with a soft cloth or wipe, thereby removing dead skin cells and debris from the skin surface and unclogging pores while leaving smooth moisturized exposed new skin.

A further exemplary embodiment provides a particulate-free microdermabrasion formulation that includes a hydrophilic, polymer composition which includes a cross-linked polyacrylate gel effective as a stabilizer and viscosity increasing agent. It further also contains a neutralizer that includes tri-ethanolamine; an ionic salt; a nonionic surfactant; a skin moisturizing composition; and water. The formulation which has a pH in the range about 6 to about 8, forms a thin layer on the surface that penetrates into pores of the skin surface. The thin layer sloughs off upon light rubbing thereby removing dead skin cells and debris from the skin surface and from pores in sloughed-off fragments of the layer to leave smooth and moisturized exposed new skin.

In exemplary embodiments, the particulate-free microdermabrasion formulations are free of chemical skin-irritants, free of chemical compositions that may cause skin irritation, such as idebenone and/or its derivatives, and free of anti-oxidants.

EXAMPLE

The following example is illustrative and does not limit the scope of the invention in any way. It is intended to provide a particular exemplary method of making an exemplary embodiment of the particulate-free microdermabrasion formulation, but does not limit the available methods that a person of ordinary skill in the art may devise, upon reading this disclosure.

Figure 3:
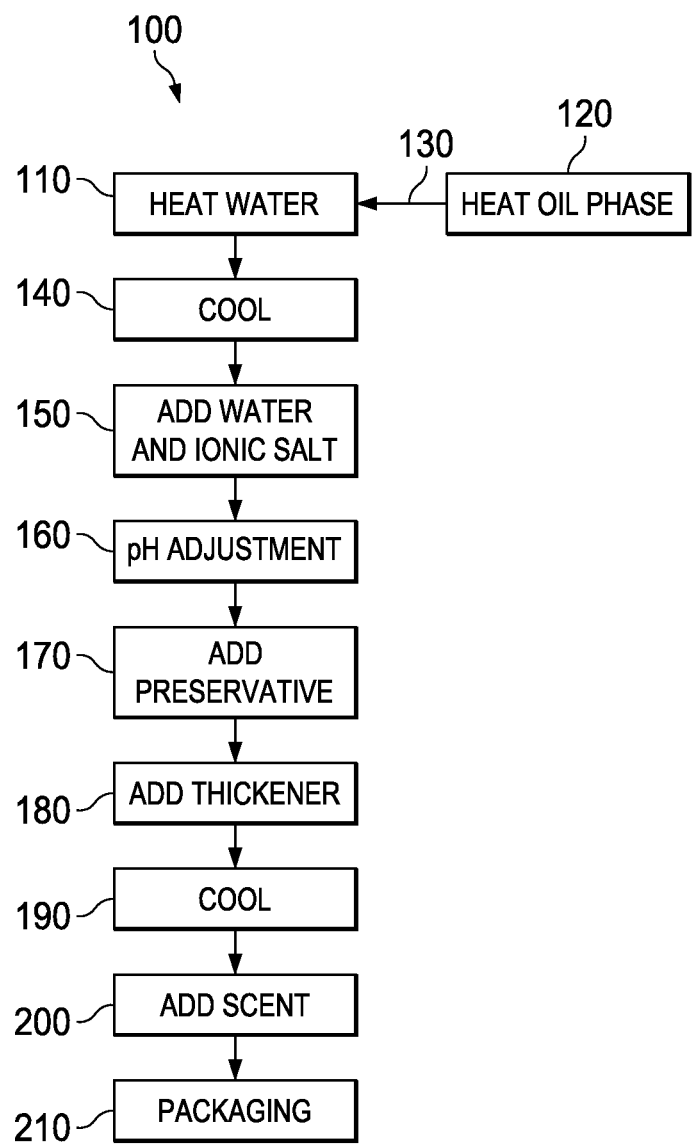
FIG. 3 is an exemplary embodiment of a process flow diagram showing the steps in making an exemplary embodiment of the formulation.

An exemplary batch process 100 for making a particulate free microdermabrasion formulation is illustrated in FIG. 3. An exemplary batch of the particulate-free microdermabrasion formulation was prepared as described in this example. The relative proportions of each component is presented as a weight percent (wt. %) of the final formulation prepared.

The water (48.55 wt. %) was heated in a first stainless steel jacketed kettle equipped with a homogenizer to the range 70-75° C., in step 110.

In a separate smaller kettle, the following were heated together in step 120 with gentle mixing to 70-75° C., as an "oil phase:"

| In a seperate kettle, the following were heated together in step 120 with gentle mixing to 70-75° C., as an "oil phase:" | |
|---|---|
| Pelemol ® IN-2 (PELEMOL is a registered trademark of Phoenix Chemical Inc.) | 6.5 wt. % |
| Pelemol ® 89 (ethylhexyl isononanoate) | 6.5 wt. % |
| Almond oil | 13.5 wt. % |
| Polysobate 60 | 2.50 wt. % |
| Sorbitan Sterate | 2.50 wt. % |

When the two kettles have each reached the desired temperature range, the oil phase was added to the water in the first kettle, in step 130, while homogenizing, for about 15 minutes.

Once the mixture had homogenized, cooling of the first kettle commenced in step 140, and additional water and sodium chloride was added in step 150. Next, triethanolamine was added in step 160, while mixing, in sufficient quantity (which was about 3 wt. %) to neutralize the pH of the mixture. A preservative system, Tristat ECO (1.50 wt. %) was then added in step 170, while continue to mix for about 5 minutes. Carbopol® 934 (3.50 wt. % produced the desired viscosity) as a thickener was added slowly, while mixing, in step 180. The batch was then cooled to 35-30° C., in step 190.

In a penultimate step 200, a scent, such as Actiphyte of Lavender GL, Actiphyte of Chamomille GL and Actiphyte of Rosemary GL were added, at 0.1 wt. % each. A sample was taken for quality control checking. After that, the prepared batch of the formulation would have been packaged in step 210.

While at least one exemplary embodiment has been presented in the foregoing detailed description section, it should be appreciated that many variations exist. It should also be appreciated that the exemplary embodiments are only examples, and are not intended to limit the scope, applicability, or configuration of the claimed inventions in any way. Rather, the foregoing detailed description provides a convenient road map for those of ordinary skill in the art to implement exemplary embodiments. It should be understood that various changes can be made in the function and arrangement of elements described herein without departing from the scope of the patent claims listed below, including the legal equivalents of these patent claims.

The invention claimed is:

1. A particulate-free microdermabrasion formulation comprising:
   a cationic surfactant an ionic surfactant in an amount from about 0.5 to about 5.0 wt. %;
   an ester or natural oil;
   an ionic salt;
   a viscosity increasing agent;
   a neutralizer; and
   water;
   wherein the particulate-free microdermabrasion formulation is free of chemical skin irritants, free of acids, free of abrasive particulates, and free of enzymes, has a pH of between about 6.0 and about 8.0, and wherein upon application to skin surface, the particulate-free microdermabrasion formulation forms a thin layer that penetrates into pores of the skin surface, the thin layer sloughing off upon light rubbing thereby removing dead skin cells and debris from the skin surface.

2. The particulate-free microdermabrasion formulation of claim 1, wherein the formulation includes from about 25 wt. % to about 50 wt. % of an ester or natural oil.

3. The particulate-free microdermabrasion formulation of claim 1, wherein the particulate-free microdermabrasion formulation includes from about 0.1 wt. % to about 5.0 wt. % of the ionic salt.

4. The particulate-free microdermabrasion formulation of claim 1, further comprising from about 0.5 wt. % to about 5.0 wt. % of a moisturizer.

5. The particulate-free microdermabrasion formulation of claim 1, wherein the particulate-free microdermabrasion formulation further comprises a preservative.

6. A particulate-free microdermabrasion formulation comprising:
  from about 0.10 to about 10 wt. % of a surfactant;
  from about 0.10 to about 5.0 wt. % of an ionic salt;
  a natural organic oil;
  from about 0.1 wt. % to about 7.5 wt. % of a hydrophilic polymer;
  triethanolamine; and
  water;
  wherein the particulate-free microdermabrasion formulation is free of chemical skin irritants, free of acids, free of abrasive particulates, and free of enzymes, and has a pH in the range from about 6 to about 8; and wherein upon application to skin surface, the particulate-free microdermabrasion formulation forms a thin layer that penetrates into pores of the skin surface, the thin layer sloughing off upon light rubbing thereby removing dead skin cells and debris from the skin surface to leave smooth and moisturized exposed new skin.

7. The particulate-free microdermabrasion formulation of claim 6, wherein the particulate-free microdermabrasion formulation includes from about 0.1 wt. % to about 2.5 wt. % of the ionic salt.

8. The particulate-free microdermabrasion formulation of claim 6, wherein the surfactant comprises from about 5.0 wt. % to about 7.5 wt. %.

9. A particulate-free, acid-free, and enzyme-free microdermabrasion formulation comprising:
  from about 0.10 to about 7.5 wt. % of a viscosity increasing agent;
  a neutralizer;
  an ionic salt in an amount ranging from about 0.10 to about 5.0 wt. %;
  a nonionic surfactant in an amount ranging from about 0.01 to about 10.0 wt. %;
  a natural organic oil; and
  a preservative;
  wherein the particle-free, chemical skin irritant-free, acid-free and enzyme-free formulation has a pH in the range from about 6 to about 8 and wherein upon application to skin surface, the particle-free, chemical skin irritant-free, acid-free and enzyme-free formulation forms a thin layer on the skin surface and penetrates into pores of the skin surface, the thin layer sloughing off upon light rubbing thereby removing dead skin cells and debris from the skin surface in sloughed off layer fragments to leave smooth and moisturized exposed new skin.

10. The particulate-free, acid-free, and enzyme-free microdermabrasion formulation of claim 9, where the particle-free, chemical skin irritant-free, acid-free and enzyme-free formulation is in the form of a gel or a lotion.

11. The particulate-free, acid-free, and enzyme-free microdermabrasion formulation of claim 9, wherein the particle-free, chemical skin irritant-free, acid-free and enzyme-free formulation is in the form of a cream.

12. A particulate-free microdermabrasion formulation comprising:
  from about 0.10 to about 10 wt. % of a surfactant;
  from about 0.10 to about 5.0 wt. % of an ionic salt;
  a natural organic oil;
  from about 0.1 wt. % to about 7.5 wt. % of a hydrophilic polymer;
  a hydroxide; and
  water;
  wherein the particulate-free microdermabrasion formulation is free of chemical skin irritants, free of acids, free of abrasive particulates, and free of enzymes, and has a pH in the range from about 6 to about 8; and wherein upon application to skin surface, the particulate-free microdermabrasion formulation forms a thin layer that penetrates into pores of the skin surface, the thin layer sloughing off upon light rubbing thereby removing dead skin cells and debris from the skin surface to leave smooth and moisturized exposed new skin.

\* \* \* \* \*